United States Patent
Vetter

(10) Patent No.: US 9,226,569 B2
(45) Date of Patent: Jan. 5, 2016

(54) RADIAL BRUSH

(71) Applicant: EVE Ernst Vetter GmbH, Pforzheim (DE)

(72) Inventor: Hermann Vetter, Pforzheim (DE)

(73) Assignee: EVE ERNST VETTER GMBH, Pforzheim (DE)

( * ) Notice: Subject to any disclaimer, the term of this patent is extended or adjusted under 35 U.S.C. 154(b) by 549 days.

(21) Appl. No.: 13/644,919

(22) Filed: Oct. 4, 2012

(65) Prior Publication Data

US 2013/0086764 A1 Apr. 11, 2013

(30) Foreign Application Priority Data

Oct. 6, 2011 (DE) .......................... 10 2011 114 916

(51) Int. Cl.
- A46B 3/00 (2006.01)
- A61C 3/06 (2006.01)
- A46B 9/08 (2006.01)

(52) U.S. Cl.
CPC . A46B 3/005 (2013.01); A61C 3/06 (2013.01); A46B 9/08 (2013.01); A46B 2200/3086 (2013.01)

(58) Field of Classification Search
CPC .. A46B 2200/1066; A46B 9/021; A46B 9/06; A46B 3/005; A46B 9/02; A46B 2200/3086; A46D 1/00; A61C 3/06
USPC ......... 15/187, 207.2, 230.13, 230.14, 230.16; 451/528, 532, 535
See application file for complete search history.

(56) References Cited

U.S. PATENT DOCUMENTS

| | | | | |
|---|---|---|---|---|
| 3,312,583 A | * | 4/1967 | Rochlis | 428/88 |
| 3,758,393 A | * | 9/1973 | Smith | 204/279 |
| 3,881,211 A | * | 5/1975 | Rhodes | 15/225 |
| 4,479,501 A | * | 10/1984 | Chern | 132/313 |
| 5,938,515 A | * | 8/1999 | McLain et al. | 451/528 |
| 6,616,366 B1 | * | 9/2003 | Weihrauch | 401/286 |
| 7,121,937 B2 | * | 10/2006 | Turch et al. | 451/526 |
| 2002/0132572 A1 | | 9/2002 | Lageson et al. | |
| 2004/0211018 A1 | * | 10/2004 | Canton et al. | 15/207.2 |

FOREIGN PATENT DOCUMENTS

| | | |
|---|---|---|
| DE | 1917825 U | 6/1965 |
| DE | 2413811 A | 10/1975 |
| DE | 296 08 399 U1 | 9/1996 |
| DE | 696 36 678 T2 | 9/2007 |
| EP | 1 106 102 B1 | 11/1996 |
| WO | WO 2007/081984 A1 | 7/2007 |

OTHER PUBLICATIONS

Search Report dated Apr. 20, 2012 issued by the German Patent Office in Related German Application No. 10 2011 114 916.7 (in German—no English translation available).

* cited by examiner

*Primary Examiner* — Robert Scruggs
(74) *Attorney, Agent, or Firm* — Robert P. Michal, Esq.; Carter, DeLuca, Farrell & Schmidt, LLP

(57) ABSTRACT

A radial brush includes a disk-shaped central body and a plurality of bristles which extend away from the central body in the radial direction. The brush is embodied in such a way that, in a region adjacent to the central body in the radial direction, bristles arranged next to one another have a dividable connection to one another over a radially extending portion.

7 Claims, 2 Drawing Sheets

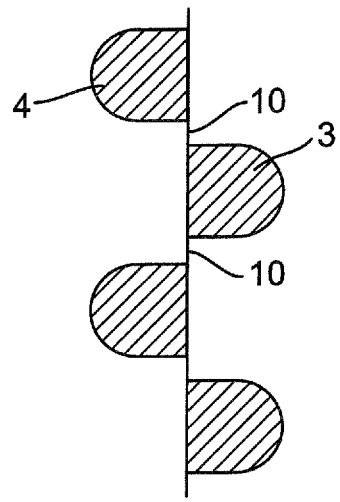
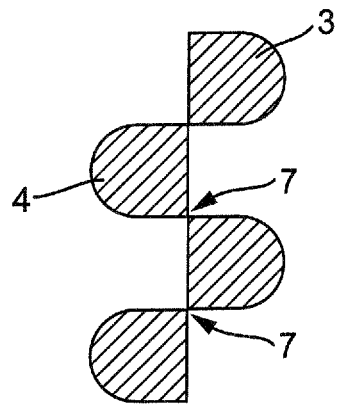
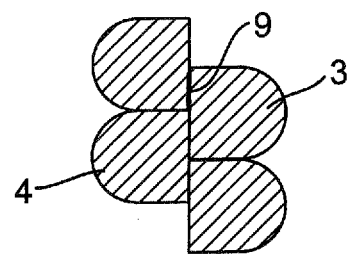
Fig. 2a        Fig. 2b        Fig. 2c
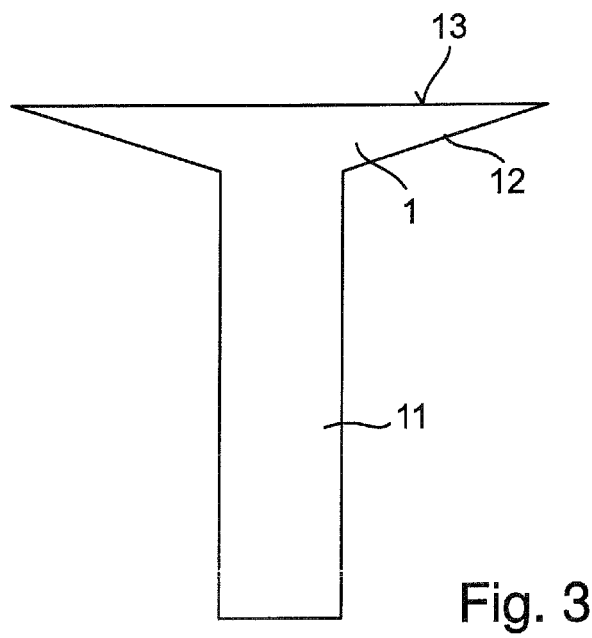
Fig. 3

RADIAL BRUSH

This application claims priority under 35 USC 119 of German Patent Application Serial No. 10 2011 114 916.7 filed Oct. 6, 2011, the entire disclosure of which is incorporated herein by reference.

The invention relates to a radial brush with a disk-shaped central body having a plurality of bristles which extend away from the central body in the radial direction.

Brushes of this type are known, for example, from US 2002/0132572 A1 or WO 2007/081984.

They are used, for example, for cleaning, grinding and polishing operations in dental technology or in jewelry production, etc.

It is essential that such radial brushes are intended to have in this case both a sufficient cleaning or grinding or polishing effect and a sufficient service life.

A good effect is achieved in particular if the bristles are relatively stiff. Such a stiffness is achieved, in particular, by a short length of the bristles.

However, since bristles are shortened during their use, short bristles have the disadvantage of only a short service life. In order to achieve a longer service life, the bristles must therefore be designed to be longer. However, the longer bristles in turn are relatively flexible and soft and thus do not achieve the desired cleaning action.

It is therefore the object of the present invention to develop a radial brush as described above such that it both has a longer service life and is combined at the same time with a continuously good cleaning, grinding or polishing performance.

This object is achieved according to the invention in that, in a region adjacent to the central body in the radial direction, bristles arranged next to one another have a dividable connection to one another over a radially extending portion.

An advantage of the invention is that the bristles which extend away from the central body in the radial direction are initially supported against one another in the radially extending portion in which they are connected to one another, with the result that only the freely projecting end of the bristles which is situated radially outside of this portion is relatively freely movable.

This relatively freely movable end of the bristle then behaves like a short bristle. Consequently, the stability of the bristle is ensured during the cleaning, grinding or polishing operation, with the result that the desired effect can be achieved.

In the cleaning, grinding or polishing operation, the free ends of the bristles wear and the bristles are shortened in so doing. Owing to the resulting stiffening of the freely movable ends of the bristles, the severable connection between bristles arranged next to one another is then successively broken, with the result that the length-dependent stiffness of the bristles is maintained since the individual bristles are progressively detached from their adjacent bristles and thus successively separate.

This leads to an action which is uniform in spite of wear combined at the same time with a longer service life of the radial brush.

In a preferred embodiment, the bristles are connected at least in a first segment of the radially extending portion by thin film elements resembling compression lugs extending in the circumferential direction and which merge in particular in one piece into the bristles. These film elements support the bristles in the circumferential direction such that the bristles can deflect somewhat only in the axial direction, whereby a certain stiffening of the bristles is achieved.

Through the design of the thickness of the film elements it is also possible to influence the tear behavior of these film elements, with the result that the wear behavior of the brush can be determined.

In a further preferred embodiment, in a first segment situated radially further outwardly the length of the film elements between bristles arranged next to one another as measured in the circumferential direction reduces inwardly in the radial direction, down to a length of zero. Here, two bristles arranged next to one another in the circumferential direction contact one another.

From this contact point further radially inwardly, the length of the connection of two bristles situated next to one another as measured in the circumferential direction of the brush then increases in a second segment situated radially further inwardly. In other words, the length of the severable connection as measured in the circumferential direction is shorter radially further outwardly and longer radially further inwardly in this second segment. Here, the bristles also lie next to one another in the axial direction in this second segment, with the result that the connection between two adjacent bristles is no longer produced between the bristles via film elements extending in the circumferential direction of the brush but, as it were, by means of direct contact of the bristle surfaces facing one another in this segment.

Consequently, with further increasing wear and thus with further progressing shortening of the bristles, a slow disconnecting of the connection between adjacent bristles is achieved in a controlled manner, this connection thus not opening rapidly or abruptly over the entire height of the radial portion.

Such a configuration can be achieved in particular if bristles arranged next to one another are offset with respect to one another both in the axial direction and in the circumferential direction. Bristles arranged next to one another in each case are thus, as it were, "staggered."

From a manufacturing point of view, it is particularly advantageous here if the bristles are arranged in two planes spaced apart from one another in the axial direction. In this case, these planes are either substantially radially oriented or describe conical lateral surfaces such that, as it were, a brush results which is "oblique" on at least one side.

In a particularly preferred embodiment, the bristles have in the inwardly radial direction a uniform or increasing cross section. This means that with increasing wear, in particular, there is an increasing stiffness of the respectively freely projecting bristle ends with a resulting permanently good cleaning, grinding or polishing performance.

Preferably, the bristles arranged next to one another are connected to one another via mutually facing planar surfaces in the region in which they also lie next to one another in the axial direction. Such a design is easy to manage from a manufacturing point of view.

In particular, the central body and the bristles can also be produced in one piece with one another. This has the advantage that the central body and the bristles can be produced in one operation, with the result that the production times for a corresponding radial brush are shortened.

Further advantages and features of the invention will become more apparent from the following description of an embodiment, in which FIG. 1 shows a plan view of a radial brush according to the invention;

FIG. 2 shows sections at different radial positions through two bristles arranged next to one another;

FIG. 3 shows a silhouette of a brush having a special axial orientation of the bristles.

Figure 1:
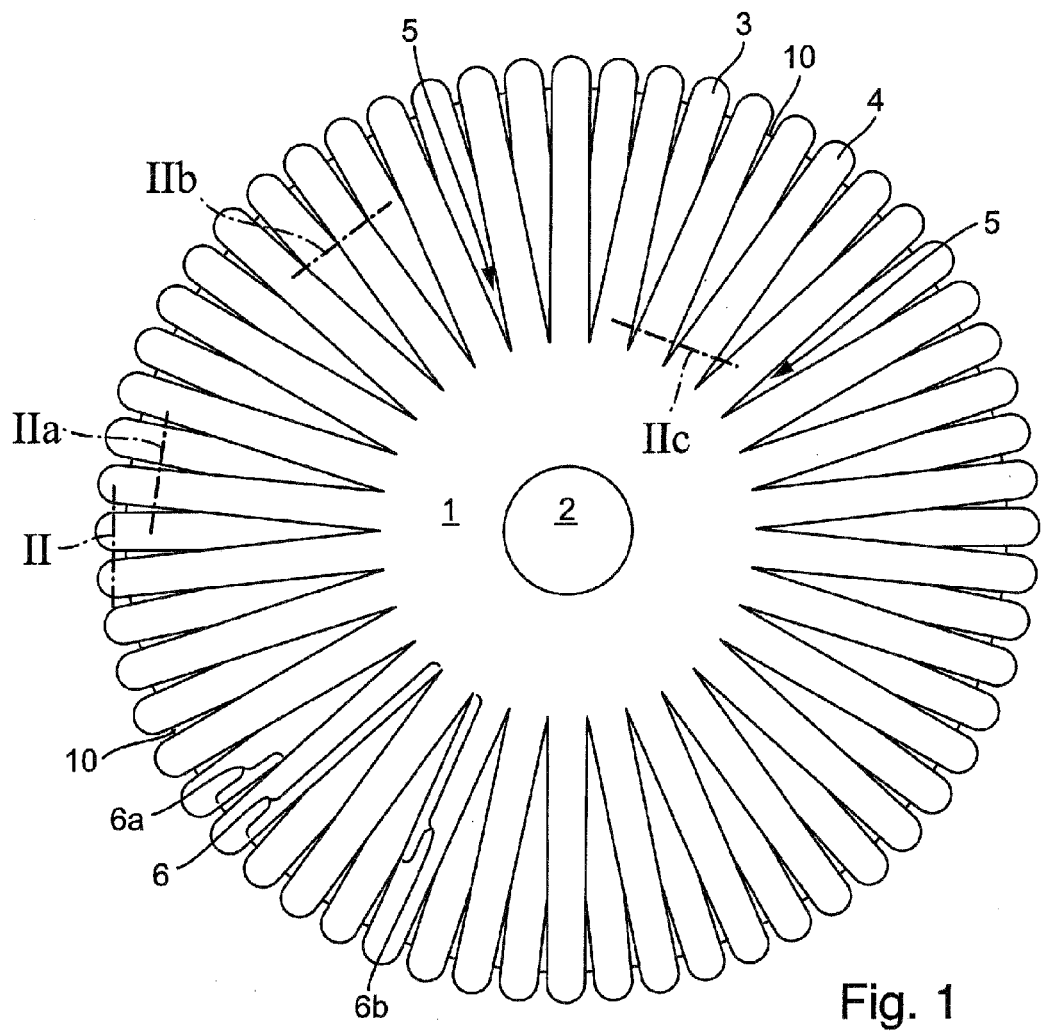
FIG. 1 depicts a radial brush in plan view.

It comprises a substantially disk-shaped central body 1 in whose center can be found a receiving hole 2. However, it is also possible, instead of a corresponding receiving hole 2, to provide a fixedly mounted shaft (as is represented in FIG. 3) or else to design this radial brush such that it can be plugged onto a shaft via a corresponding design of the receiving hole 2.

A plurality of bristles 3, 4 extend away in the radial direction from the central body 1 over the circumference thereof. Here, the bristles 3, 4 at their base 5 merge in one piece into the central body 1 at their base 5, respectively.

The central body 1 and the bristles 3, 4 consist, for example, of a very wear-resistant flexible material, such as, in particular, a synthetic or natural rubber or rubber-like material or plastic which is impregnated or interspersed with grinding or polishing substances of different particle size, for example diamond, silica or aluminum oxide, pumice, etc.

The bristles present are arranged around the central body 1 with a constant pitch angle which is uniform over the circumference, wherein, in the example represented here in FIG. 1, in each case two bristles arranged next to one another are offset with respect to one another both in the axial direction and in the circumferential direction. Here, the bristles are arranged on the front side and the rear side of the central body in two parallel planes spaced axially apart from one another and are here in each case offset relative to one another by half a pitch angle.

In the region 6, which is adjacent to the central body 1 in the radial direction, these bristles arranged next to one another are connected to one another such that they can be divided. This is represented in sections in FIG. 2. In a radially outwardly situated first segment 6a of the region 6, the two bristles here are connected by a thin film element 10 resembling a compression lug extending in the circumferential direction, whereas, in the example represented here, in the radially further inwardly situated second segment 6b of the region 6 the bristles 3, 4 are situated directly next to one another in the axial direction and here are connected to one another.

In FIG. 1, a section is taken at the point II. At this point, the two bristles 3 and 4 arranged next to one another are offset with respect to one another in the axial direction, but have absolutely no contact with one another. In this region, the free ends of the bristles 3, 4 are thus freely movable.

In FIG. 1, a section IIa is taken which is positioned in the first segment 6a in which the bristles 3, 4 lying next to one another are connected by a film element 10. This film element is like a compression lug and merges in one piece into the bristles 3 and 4, respectively. When the free bristle ends as they are present in the region of the section II wear, the resulting stiffening of the free bristle ends will cause the film element 10 to tear and then the free bristle ends which are shortened by means of wear are released from one another, with the result that the then radially outwardly situated ends of the bristles 3, 4 are free of one another again so that they can achieve the desired cleaning, grinding or polishing effect. As long as the film element 10 has not yet split, the bristles 3, 4 still mutually support one another by means of this film element, in particular in the circumferential direction.

In its form represented in plan view, the film element 10 is substantially triangular. The two longitudinal sides of the triangle are here identical to the edges of the bristles 3 and 4 which extend in the first segment 6a. The tip of this triangle is at the transition point 7 between the first segment 6a and the second segment 6b of the region 6. The section IIb in FIG. 1 also runs through this point 7.

In the region of the section IIb which is depicted in FIG. 1, the situation represented in FIG. 2b arises in which the two bristles 3, 4 are connected precisely to one another. The connection or transition point 7 is thus very short (virtually punctiform) in the circumferential direction 8 and can easily tear or split. This tearing takes place when the bristles 3, 4 wear further and thus lose their length, their ends thus come to lie in the first segment 6a and the film elements 10 have already completely torn. As a result of the wear, the free ends of the bristles continue to become shorter and thus also stiffer. This stiffness leads to a holding force which acts on the foot of the free end of the bristle and which, starting from a certain size, leads to a tearing of the dividable connection at the transition point 7, this tearing then progressing through the second segment 6b of the region 6.

Further inwardly in the radial direction, the bristles 3, 4 overlap in the circumferential direction 8 over a relatively large length 9, as is depicted in section IIc or in FIG. 2c. The section IIc is situated close to the base 5 of the bristles 3 and 4 at which the latter merge into the central body 1. This length 9 tears only when the bristles 3, 4 are significantly worn and thus significantly shortened and thus also are significantly stiffer.

The dividable connection between in each case adjacent bristles consequently tears in only a slowly progressing manner and thus, with progressing wear which is measured in the radial direction, the free ends of the bristles which extend to the start of the (remaining) connection between two bristles will not be reduced in their length to the same extent.

Even if the shape of the cross section of the bristles 3, 4 is represented as half-round in FIG. 2, the bristles 3, 4 can also have other cross-sectional shapes, for example being round or oval or else rectangular or square.

In the embodiment described up until now, the basic starting point has been a substantially planar configuration of the radial brush in which the bristles 3 and 4 each extend in radial planes situated parallel to one another.

However, it is also conceivable for the radial brush to be designed as represented in silhouette in FIG. 3.

In this example, a shaft end 11 is connected to the central body 1, with the adjoining bristles (not shown in detail) being inclined out of a radial plane and thus forming a conical lateral surface 12. The bristles situated on the opposite side 13 can then be inclined with a smaller inclination from the radial plane in the same direction as the conical lateral surface 12 or else lie exactly in a radial plane.

However, it is also possible for the bristles of the opposite side 13 to be inclined in the opposite direction to the inclination of the conical lateral surface 12. In that case, a radial brush which becomes thicker with increasing wear is obtained.

Apart from polyurethane, other materials are also suitable for the bristles and/or the central body, such as soft flexible or hard flexible rubbers, synthetic rubbers or plastic. Depending on the application, these are interspersed with substances having a greater or lesser grinding action.

The invention has the advantage that, by virtue of the uniformly high flexibility of the grinding or polishing bristles, it is made possible for the bristle ends to migrate in the axial direction so as to be able to polish depressions or uneven surface regions, for example, of dental crowns having cusps and fissures or occlusions.

The fact that originally the individual polishing bristles are severed only in the outermost region while they adhere to one another more strongly or are connected to one another more strongly in the central and lower region means that there results a firmer connection of the individual radial bristles in the radially inner region, this connection tearing only as a result of the continuous wear of the bristles in order then to be able to achieve the actual brush-like effect up to close to the edge of the central body 1.

The invention claimed is:

1. A radial brush comprising a disk-shaped central body and a plurality of individual bristles operatively coupled to the central body, the plurality of individual bristles each having a length extending away from a circumference of the central body in a radial direction of the radial brush, wherein, individual bristles which are arranged next to one another have a dividable connection to one another, said dividable connection comprising film elements, the film elements being in a first section of a region which is in the radial direction of the radial brush distally located with respect to the central body, which region extends in a radial direction of the brush, and said first section of the region is less than the entire length of the individual bristles, the film elements extending in the circumferential direction of the radial brush.

2. The radial brush according to claim 1, wherein at least in a second segment of the region a length of the connection becomes longer the further, with regard to the brush, radially inwardly it is measured, said length being measured in a circumferential direction of the radial brush.

3. The radial brush according to claim 2, wherein bristles arranged next to one another are connected to one another via mutually facing planar surfaces.

4. The radial brush according to claim 1, wherein bristles which are arranged next to one another are offset with respect to one another in the axial direction and in the circumferential direction of the radial brush.

5. The radial brush according to claim 1, wherein the bristles are arranged in two planes, said planes being spaced apart from one another in the axial direction of the radial brush.

6. The radial brush according to claim 1, wherein the bristles have in the radial inwardly direction uniform or increasing cross section.

7. The radial brush according to claim 1, wherein the central body and the bristles are produced in one piece with one another.

* * * * *